(12) United States Patent
Mickles et al.

(10) Patent No.: US 11,481,395 B2
(45) Date of Patent: Oct. 25, 2022

(54) DATABASE QUERY PROCESSING SYSTEM FOR BLOOD DONATION TRACKING SYSTEM

(71) Applicant: FENWAL, INC., Lake Zurich, IL (US)

(72) Inventors: Kathleen Mickles, Lake Zurich, IL (US); Dale Meixelsperger, Gurnee, IL (US)

(73) Assignee: FENWAL, INC., Lake Zurich, IL (US)

( * ) Notice: Subject to any disclaimer, the term of this patent is extended or adjusted under 35 U.S.C. 154(b) by 696 days.

(21) Appl. No.: 15/134,718

(22) Filed: Apr. 21, 2016

(65) Prior Publication Data

US 2016/0328521 A1 Nov. 10, 2016

Related U.S. Application Data

(60) Provisional application No. 62/205,076, filed on Aug. 14, 2015, provisional application No. 62/159,007, filed on May 8, 2015.

(51) Int. Cl.
*G06F 16/2455* (2019.01)
*G16H 10/60* (2018.01)
*G16H 40/20* (2018.01)

(52) U.S. Cl.
CPC ........ *G06F 16/2455* (2019.01); *G16H 10/60* (2018.01); *G16H 40/20* (2018.01)

(58) Field of Classification Search
CPC ............. G06F 19/322; G06F 17/30477; G06F 16/2455; G16H 40/20; G16H 10/60
USPC ............................................................ 705/3
See application file for complete search history.

(56) References Cited

U.S. PATENT DOCUMENTS

| 5,496,265 A | 3/1996 | Langley et al. |
| 5,658,240 A | 8/1997 | Urdahl et al. |
| 6,581,011 B1 | 6/2003 | Johnson et al. |

(Continued)

FOREIGN PATENT DOCUMENTS

| WO | WO2006118614 | 11/2006 |
| WO | WO2007108855 | 9/2007 |
| WO | WO2008051630 | 5/2008 |

OTHER PUBLICATIONS

European Search Report and Opinion, Application No. 16168288.5 dated Aug. 23, 2016, 7 pages.

(Continued)

*Primary Examiner* — Robert A Sorey
*Assistant Examiner* — Kimberly A. Sass
(74) *Attorney, Agent, or Firm* — Becker Patent Law, LLC

(57) ABSTRACT

A database query processing system for blood donation tracking includes a database, a network interface circuit and a processing circuit. The database stores records for a plurality of blood donors, each record comprising an amount of a blood component the blood donor has donated. The processing circuit determines an amount of a blood component a first donor may donate based on records for a plurality of donations made by the first blood donor and based on a limit of an amount of blood component the donor may donate in a predetermined period of time. The processing circuit further receives a request for the amount of the blood component the first donor may donate and transmits the amount of the blood component the first donor may donate to the remote computing device.

19 Claims, 11 Drawing Sheets

(56) References Cited

U.S. PATENT DOCUMENTS

| | | | |
|---|---|---|---|
| 7,072,769 B2* | 7/2006 | Fletcher-Haynes | A61M 1/3496 702/21 |
| 7,354,415 B2 | 4/2008 | Bainbridge et al. | |
| 7,430,478 B2 | 9/2008 | Fletcher-Haynes | |
| 2003/0004751 A1* | 1/2003 | Ng | G06Q 10/08 705/2 |
| 2004/0199098 A1* | 10/2004 | Pierce | A61M 1/02 604/4.01 |
| 2005/0060246 A1* | 3/2005 | Lastinger | G06Q 10/087 705/28 |
| 2005/0209883 A1* | 9/2005 | Fletcher-Haynes | A61M 1/3693 705/2 |
| 2010/0049542 A1 | 2/2010 | Benjamin | |
| 2012/0010062 A1* | 1/2012 | Fletcher | A61M 1/3693 494/10 |
| 2012/0038651 A1 | 2/2012 | Case | |
| 2015/0186834 A1 | 7/2015 | Mickles et al. | |

OTHER PUBLICATIONS

Cobe Trima Automated Blood Component Collection System, Operator's Manual, Version 3.0, (c) 1997, 26 pages.

Request for Examination in European Application No. 16168288.5 dated May 8, 2017, 19 pages.

Communication pursuant to Article 94(3) EPC in European Application No. 16168288.5 dated Mar. 21, 2018, 6 pages.

Maikowski & Ninneman letter in European Application No. 16168288.5 dated Sep. 3, 2018, 16 pages.

Communication pursuant to Article 94(3) EPC in European Application No. 16168288.5 dated Oct. 27, 2020, 6 pages.

Barker Brettell letter in European Application No. 16168288.5 dated May 4, 2021, 12 pages.

Communication pursuant to Article 94(3) EPC in European Application No. 16168288.5 dated Feb. 3, 2022, 8 pages.

Barker Brettell letter in European Application No. 16168288.5 dated May 26, 2022, 16 pages.

* cited by examiner

DATABASE QUERY PROCESSING SYSTEM FOR BLOOD DONATION TRACKING SYSTEM

CROSS-REFERENCE TO RELATED APPLICATIONS

This application claims the benefit of U.S. Provisional Application No. 62/205,076, filed Aug. 14, 2015 and U.S. Provisional Application No. 62/159,007 filed May 8, 2015, both of which are incorporated by reference herein in their entireties.

BACKGROUND

The present application relates generally to a blood donor history record system. The present application relates more specifically to systems and methods for improving the selection of blood components to be collected during a donation.

Blood components, such as red blood cells, platelets, and plasma, are used in transfusion facility settings to treat injury and disease. For example, red blood cell transfusions are often performed for patients suffering from anemia, platelet transfusions are performed to limit bleeding and hemorrhaging in patients with excessive bleeding, bleeding disorders, or hematologic malignancies, and plasma, platelets, red blood cells, and/or whole blood may be transfused during surgical procedures to replace blood or blood components that have been lost.

A blood component collection facility schedules blood component collections for blood donors. Blood donors are limited by the number of blood donations and blood loss that may occur in a predetermined period of time following regulated guidelines. When scheduling a donation, blood component collection facilities consider the donation limits of the donor along with other factors, such as but not limited to, the needs of the facility or its customers, the components previously collected from a particular donor, the available blood donation equipment, etc. The number of factors that a scheduler must consider makes the scheduling task difficult.

BRIEF DESCRIPTION OF THE DRAWINGS

Exemplary embodiments are described below with reference to the accompanying drawings, wherein like numerals denote like elements, and.

DETAILED DESCRIPTION OF ILLUSTRATIVE EMBODIMENTS

One or more embodiments described herein may improve the management of inventories of blood components.

One of more embodiments may optimize the donor base management to align with demand, lower blood center cost, and/or to otherwise meet manufacturer goals.

One or more embodiments may improve the predictability, efficiency, and/or automation of blood component supply chains.

One or more embodiments may provide tools for tracking blood component inventories, forecasting blood component demand, and coordinating donations to better match new supply to current demand.

One or more embodiments may make the scheduling and/or blood component selection process easier on a person tasked with scheduling a blood donation.

One or more embodiments may reduce errors associated with scheduling a donor for a donation that exceeds the donor's donation limit in a predetermined period of time.

Figure 1:
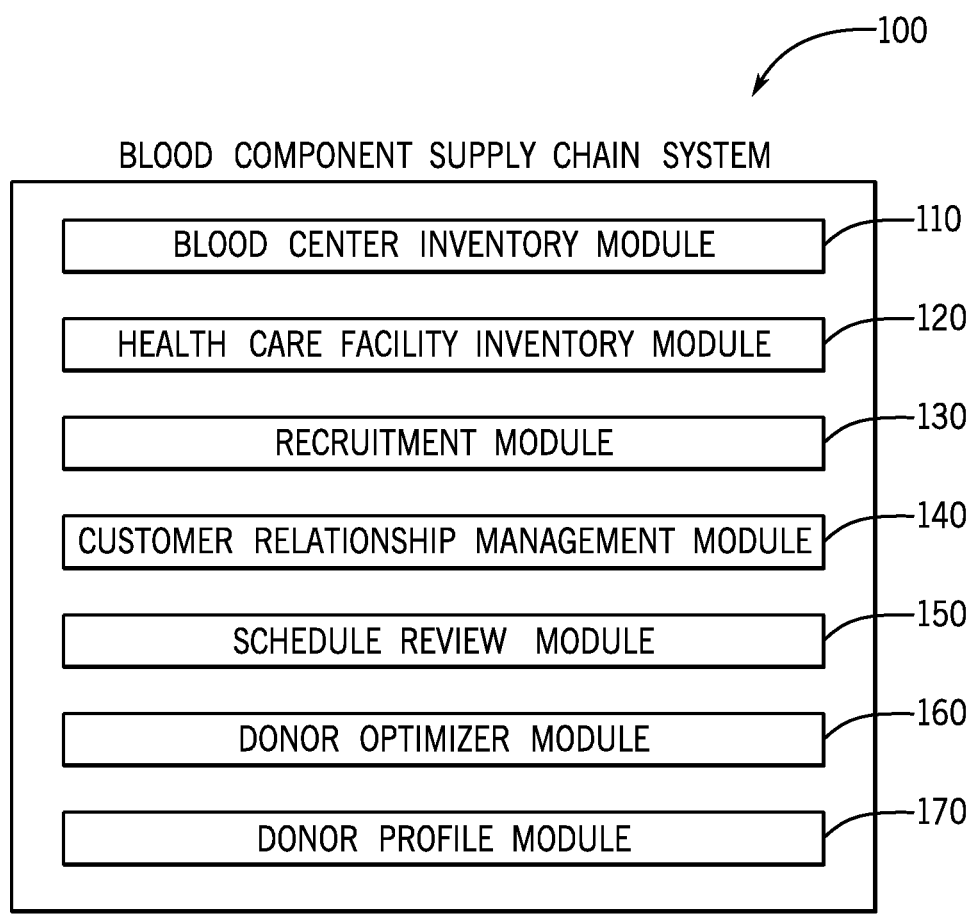
FIG. 1 is a general schematic block diagram depicting various functional modules of a blood component supply chain management system in accordance with one exemplary embodiment.

Referring now to FIG. 1, some embodiments of a blood component supply chain management system 100 include a Blood Center Inventory Module 110. Such a module tracks the inventory of a blood center allowing the blood center to know what supply of blood components it has in its reserves. In some embodiments, a log of the blood center's inventory is stored in a computer database. Blood component units added to the inventory are added to the inventory log and blood component units removed from the inventory are removed from the inventory log. The inventory log includes details about the blood component units stored in the blood center's inventory. For example, in some embodiments, the inventory log at least includes a unique identifier, the component type, the blood type, and the expiration date for each blood component unit. As further example, an entry for a particular blood component bag may list: a number or other code uniquely identifying the bag; an indication of whether the bag contains whole blood, plasma, platelets, RBC, etc. (i.e., the component type); an indication of whether the bag contains components from A, B, AB, or O blood (i.e., the blood type); and the date at which the blood component is no longer safe for transfusion into humans (i.e., the expiration date). Additional blood component characteristics, including the date the blood component was donated, may also be included. In some embodiments, some or all such information is contained within, embedded within, or encoded within the unique blood component identifier. In some embodiments, some or all such information is contained within, embedded within, or encoded within a bar code, RFID code, or other scannable or graphical representation of data.

Blood Component Supply Chain Management

Returning to FIG. 1, some embodiments of a blood component supply chain management system 100 include a Health Care Facility Inventory Module 120. Such a module enables automated tracking of blood component units even after the units leave the control of the blood center, for example, once the units enter a health care facility (e.g., hospital, surgical care unit, etc.). Using the blood component supply chain management system 100 of some embodiments, health care facilities can directly and electronically order particular blood components as the needs arise. Additionally or alternatively, in some embodiments, health care facilities can set up the system such that orders for particular blood components are placed automatically by the system when current supplies fall below a specified amount. That specified amount may be a default amount determined by the system or specified by the health care facility. In some embodiments, health care facilities can store financial data in the system so that payments can be automated at the time of ordering.

The blood component supply chain management system 100 of FIG. 1 also includes a Recruitment Module 130. In various embodiments, the Recruitment Module 130 facilitates a blood center's recruitment efforts, particularly, for example, when a current or upcoming demand is identified by the system. The module may improve the efficiency of the recruitment processes. The module may automate all or portions of the recruitment process. Advantageously, in various embodiments, the Recruitment Module 130 identifies the best, or recommended, donors to recruit. Particularly when demand for a particular blood component exists or is imminent, blood centers would benefit from recruiting reliable donors capable of donating a maximum allowable amount of the particular needed blood component. Doing so would increase the speed at which a blood center can generate supply to fill demand. Thus, in some embodiments, the system analyzes the donor profiles of past donors, comparing the blood center's past donors along one or more metrics, to identify recommended donors. (Donor profiles may be created for each donor, and the creation of such profiles is discussed in more detail below.)

Recommended donors (i.e., optimal donors) often have one or more of the following characteristics: they have a desired blood type; they donated insufficiently in the past so as to be eligible to donate again; the number of times they donated within the past year is such that they are eligible to donate again; they have reliably showed up to past donation appointments for which they were scheduled; they meet current regulatory donation criteria for a particular needed blood component; and they are eligible to donate the particular needed blood component based on their gender, height, and weight. Optionally, in some but not all embodiments, the donors have successfully donated the particular needed blood component or other blood component in the past. In some embodiments, the system first identifies which of the blood center's past donors are currently eligible to donate. The eligible donors may then be compared and those with the largest number of desirable attributes selected as recommended donors.

In various embodiments, the Recruitment Module 130 may work in conjunction with a Customer Relationship Management (CRM) Module 140 to facilitate the recruitment process. Once recommended donors are identified, the CRM may be utilized to identify contact information for the recommended donors and coordinate efforts for reaching out to the recommended donors. In some embodiments, the system, via the Recruitment Module 130 and/or the CRM Module 140 generates automated emails, text messages, automated phone calls, or other electronic communications, which are sent to the recommended donors to recruit them to donate again. The CRM Module of some embodiments additionally provides a platform through which blood center staff and/or donors can electronically schedule blood collection appointments. The platform may also allow blood drive organizers to electronically schedule blood drives, such as, for example, through a web-based or application interface.

Some embodiments of a blood component supply chain management system 100 also include a Schedule Review Module 150. In some embodiments, the Schedule Review Module 150 improves a blood center's ability to efficiently collect a particular blood component in current or imminent demand by making modifications to scheduled appointments as demand changes, so that the blood component that is ultimately collected is a blood component that is needed. In some embodiments, when a need arises for a particular blood component, the Schedule Review Module 150 allows blood center staff to identify donors with upcoming appointments who can help the blood center meet the changing needs. For example, the module of some embodiments reviews logs of scheduled appointments, identifies appointments that are for the collection of a blood component that is not in particular demand, and optionally, suggests modifications to the appointments such that a needed blood component is instead collected at the appointment optimizing the appropriate collection device technology. In some embodiments, the module first reviews a donor's profile to ensure the donor is eligible to donate a needed blood component.

The blood component supply chain management system 100 of various embodiments also includes a Donor Optimizer Module 160. Advantageously, the Donor Optimizer Module 160 may provide real-time modifications in blood component collections to match real-time needs. Collection recommendations are provided to optimize the donor's potential based on defined criteria for the collection device technology. The module of some embodiments identifies donors on the day of donation, reviews the blood component the donor is scheduled to donate, and may suggest modifications if a demand for a blood component arises that is different than the blood component the donor is scheduled to provide or if the system detects that the scheduled collection is not optimized. In some embodiments, the suggested modification is presented to a user, such as a donor or a blood center staff member, at the time of collection. The Donor Optimizer Module 160 may integrate with an input device configured to receive an input from a donor, which uniquely identifies the donor. The Donor Optimizer Module 160 may also integrate with a blood collection device such that if a user selects to make a suggested modification, the blood collection device receives instructions to collect the appropriate blood component.

The blood component supply chain management system 100 of various embodiments may further include a Donor Profile Module 170. Past donors and scheduled donors have donor profiles stored in the blood component supply chain management system. A donor profile can be created and edited via the Donor Profile Module 170. In various embodiments, the donor profile is a donor-specific data space within the memory of the blood component supply chain management system, which is accessible using a unique identifier.

The donor-specific data space stores data pertaining to the donor. The donor-specific data is maintained by the blood component supply chain management system and is accessible by users with proper credentials, such as a specific donor, and optionally, blood center staff. The donor profile may include: biographical data such as a donor's birth date, gender, weight, height, and blood type; and appointment history such as a log of past donations, including dates and products donated, a count of past donations, a show rate (i.e., percent of scheduled appointments the donor appeared for), etc. The donor profile may be accessible via a web-based interface or application interface, for example, to enable review of historical collections and the characteristics of scheduled donors. In some embodiments, data pertaining to each donor's past appointments (e.g., show rate, date of donation, component type and amount donated, etc.) can be aggregated for each donor or for all individuals who donated to a blood center during a particular time interval. Storing and aggregating such information in the system allows for period reviews, such as, for example, quarterly compliance reviews. In some embodiments, the donor profile is automatically edited by the system, for example, when an appointment is scheduled, when an input device detects the arrival of the donor at a donation site, and when a blood collection device records a successful collection.

System Components

The various functionality described herein may be implemented by a system comprising one or more computers, such as one or more servers coupled via a communication network to at least one or more tracking devices, one or more blood component collection devices, and one or more user workstations. One example of such a system is provided in FIG. 2 and discussed in detail below.

Figure 2:
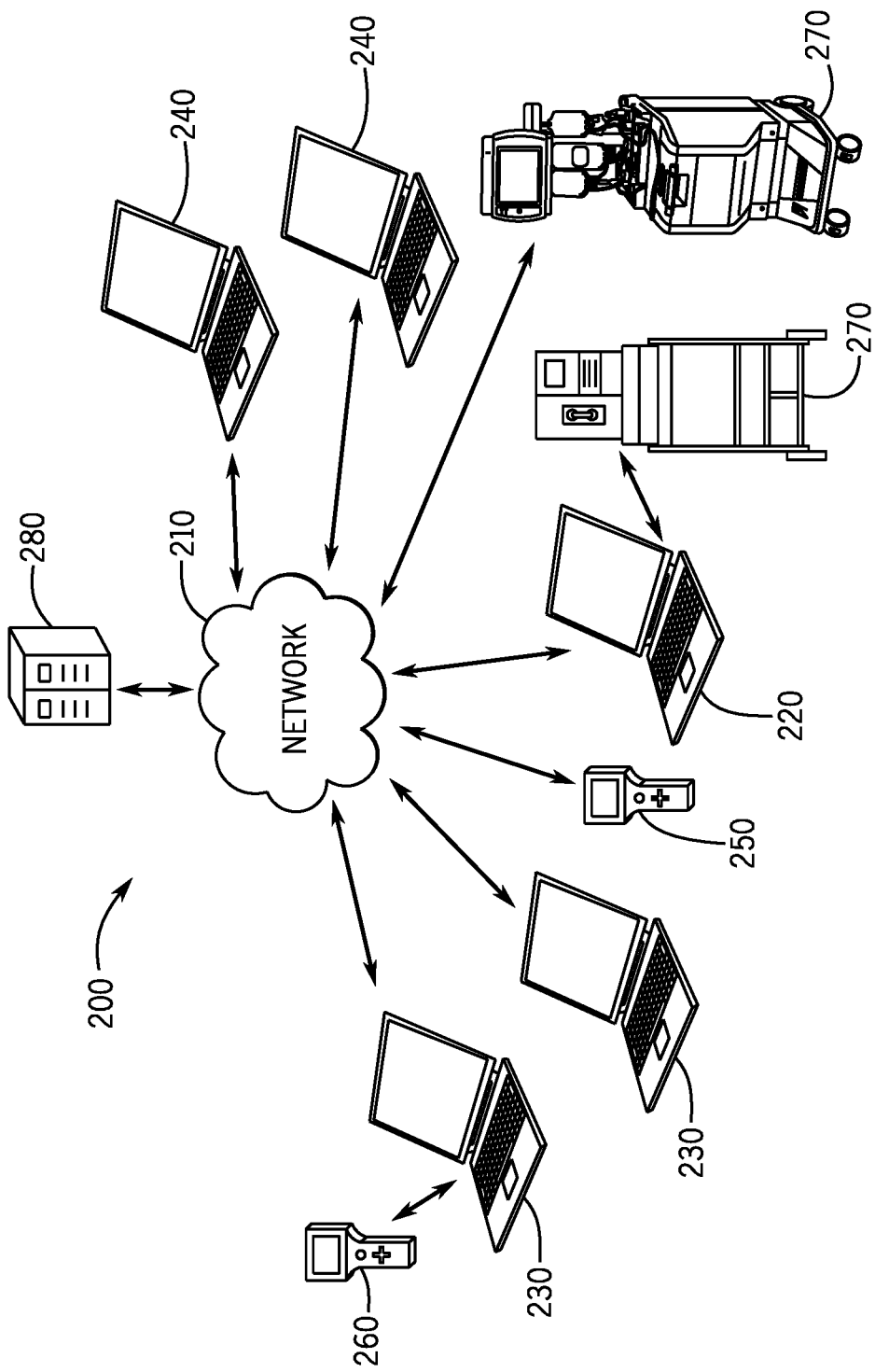
FIG. 2 is a schematic diagram of a blood component supply chain management system, depicting various components of the system and interactions between the components in accordance with another exemplary embodiment.

FIG. 2 illustrates a schematic diagram of hardware components found in embodiments of a blood component supply chain management system 200 and includes a schematic illustration of the interactions between said components. The embodiments are illustrative in nature only and various components may be added, deleted, or substituted and various different hierarchies and modes of communication between the devices may be employed. In the depicted example, the blood component supply chain management system 200 is formed of a plurality of computerized devices. The system 200 includes a communication network 210 through which some or all of the various devices communicate with one another. In some embodiments, a plurality of the devices are configured to transmit information to, and receive information from a server 280 via the communication network 210. The network can comprise one or more of a local area network (LAN), a wide area network (WAN), or other networks. In some embodiments, the network comprises a wireless communication network to which at least some of the devices are connected, such as, for example, a mobile WiMAX network, LTE network, Wi-Fi network, or other wireless network. In other embodiments, the communication between at least some of the system devices and the server 280 occurs over the Internet via a wired network, such as a DSL cable connection, or over Ethernet or an intranet.

In various embodiments, the system is accessible to users of the system via user workstations, such as workstations at a blood center 220, workstations at various health care facilities 230, and donor workstations 240. The workstations may be specialized computers configured solely for connection to the system 200, or they may be generalized computers made to perform specialized functions by way of programmed microprocessors. For example, in some embodiments, the various workstations 220, 230, and 240 are desktop computers, laptop computers, and/or mobile devices such as tablets or smartphones.

In various embodiments, the blood component supply chain management system 200 is owned, operated, or managed by, or otherwise tailored to, an individual blood center and/or health care facility. A single blood center may have a plurality of blood center workstations 220 connected to the system. Thus, while one or two workstations are depicted for each participant, it will be appreciated that the system 200 may include any number of workstations 220, 230, and 240. The system 200 may also include any number of tracking devices 250, 260 and blood collection devices 270.

In various embodiments, the server 280 includes a processor and memory, and software code is stored in the memory, which, when executed by the processor, causes the system to perform some or all of the system functions described above. In some embodiments, the server 280 includes an application server. In some such embodiments, some software code is stored in the server 280, while additional software code is stored on each other network-connected device (e.g., 220, 230, 240, 250, 260, and 270) in the form of one or more program applications. In some such embodiments, "back end" functions such as storing information sets in databases, calculations, analyses, and information retrieval is largely performed by, and coded for, within the server 280, while "front end" functions, such as the display of information on a graphical user interface (GUI), is performed by, and coded for, within the other network-connected devices. The server 280 may include a web server and various features and functionality are made possible by the software code stored within server 280. In some such embodiments, each user workstation 220, 230, 240 may include an internet browser, through which users can access, and interact with, the blood component supply chain management system 200. In various embodiments, the server 280 also includes a database server on which datasets such as inventory logs, scheduling logs, and donor profiles or records are stored. Server 280 may be formed of any suitable number of servers. For example, in some embodiments, the server 280 includes one or a plurality of application servers, one or a plurality of web servers, a cloud computing environment, and/or one or a plurality of database servers.

As depicted in FIG. 2, the various devices of the system interact with the network 210, and accordingly, each other, via two-way (forward and reverse) communication links. Each of the devices depicted in FIG. 2 may comprise one or more network interface circuits configured to receive data over a network relating to donations made by the blood donors and configured to communicate the data over the network to a remote computing device. The network interface circuits may comprise analog and/or digital electronic components configured to perform the communication functions over the one or more networks. The devices each include network interface circuits, such as input/output devices for wired communication connections (e.g., modems, network cards, external data buses, ports, etc.) and/or wireless receivers and transmitters, which allow each device to transmit and receive information.

In certain embodiments, the blood center workstation 220 has an input/output device (e.g., mouse, keyboard, touch-screen, monitor, etc.) allowing it to receive inputs from a user and display graphical outputs. Users, such as blood center staff, may enter information about the blood center's inventory, scheduling information, or information about new or potential donors. Such information is transmitted to the server 280 via the communication network 210 for storage, and optionally, for processing. Blood center staff can also use the blood center workstations 220 to send requests for, and receive, information such as: data regarding the inventory of various health care facilities, stored donor profiles, stored donor contact information, stored scheduling data, orders from health care facilities for additional blood components, and a summary of the demands for blood components and/or upcoming demands, as determined by the system from various health care facility inventories.

Similarly, donor workstations 240 also have input/output devices (e.g., mouse, keyboard, touchscreen, monitor, etc.) for receiving inputs from users and displaying graphical outputs to users. Upon request by a user through interaction with, and data input via, a GUI, the workstations 240 may receive scheduling and donor profile information stored in the server 280. Such information may be displayed to the user for review and/or editing. The workstations 240 may also transmit scheduling and/or donor profile data to the server 280 in order to add to, or update, the stored information.

As shown in FIG. 2, the system may include a plurality of tracking devices, such as the blood center tracking device 250 and the health care facility tracking device 260. Each party may have one or more tracking devices to track its inventory. In some embodiments, the tracking device 250, 260 is an RFID reader or computer kiosk including an RFID reader; in other embodiments, it may be any other suitable tracking device, such as a barcode scanner. In some embodiments, the tracking devices are electrically or wirelessly connected to a network-connected computer.

The system may include a plurality of blood collection devices 270, such as, for example, one or more of the Alyx®, CompoGuard®, Aurora, and/or Amicus® devices, manufactured by Fresenius Kabi. These devices may collect whole blood and/or certain blood components and may perform apheresis functions. In some embodiments, such devices 270 are configured for wireless communication and include a wireless receiver and transmitter. The blood collection devices 270 of various embodiments may exchange data with the server 280 via the network 210. Additionally or alternatively, a blood collection device 270 may exchange data with a blood center workstation 220 via a wired or wireless connection, and the blood center workstation 220 may exchange such information with the server 280. In various embodiments, the exchange of data between one or more blood collection devices 260 and one or more workstations 220 or servers 280 enables blood centers to: send the collection devices 270 instructions regarding what components to collect and other programming parameters, monitor machine and operator performance, and/or capture and analyze procedure data remotely.

Methods

Using some or all of the devices, components, and systems described herein, various methods may be implemented by the blood component supply chain management systems. Such methods may integrate into existing supply chain processes and improve the efficiency, predictability, and/or outcomes of the blood component supply chain. Various embodiments of the methods performed by blood component supply chain management systems include methods for tracking blood component inventories, forecasting blood component demand, and coordinating optimized donations to meet current and anticipated demand. Some systems described herein may perform all such functions together in an integrated manner. Other systems described herein may perform only one or some of the optimization methods.

Figure 4:
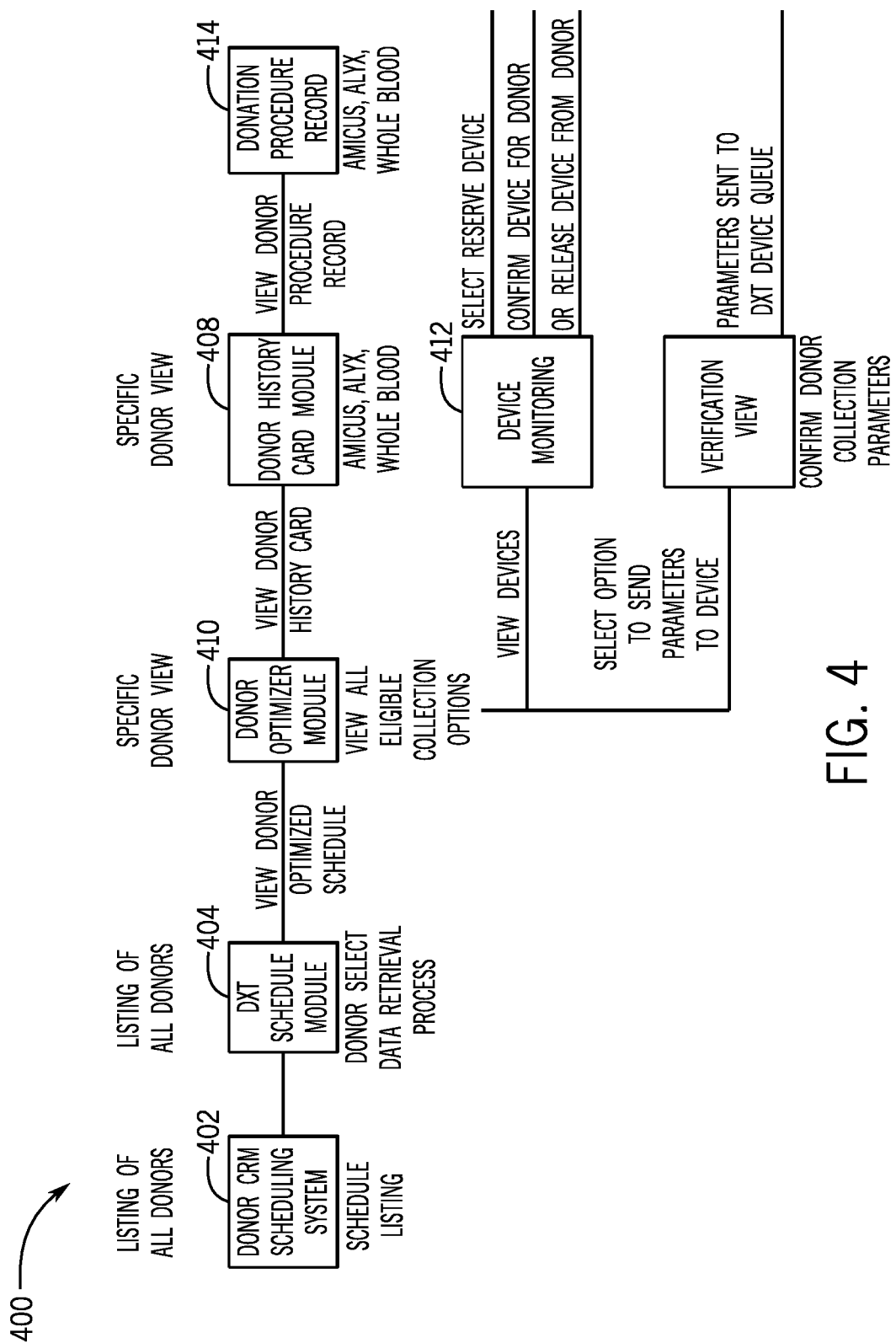
FIG. 4 is a flow diagram illustrating a sequence of steps in a process of scheduling a donation type using a computing system, according to an exemplary embodiment.
Figure 7:
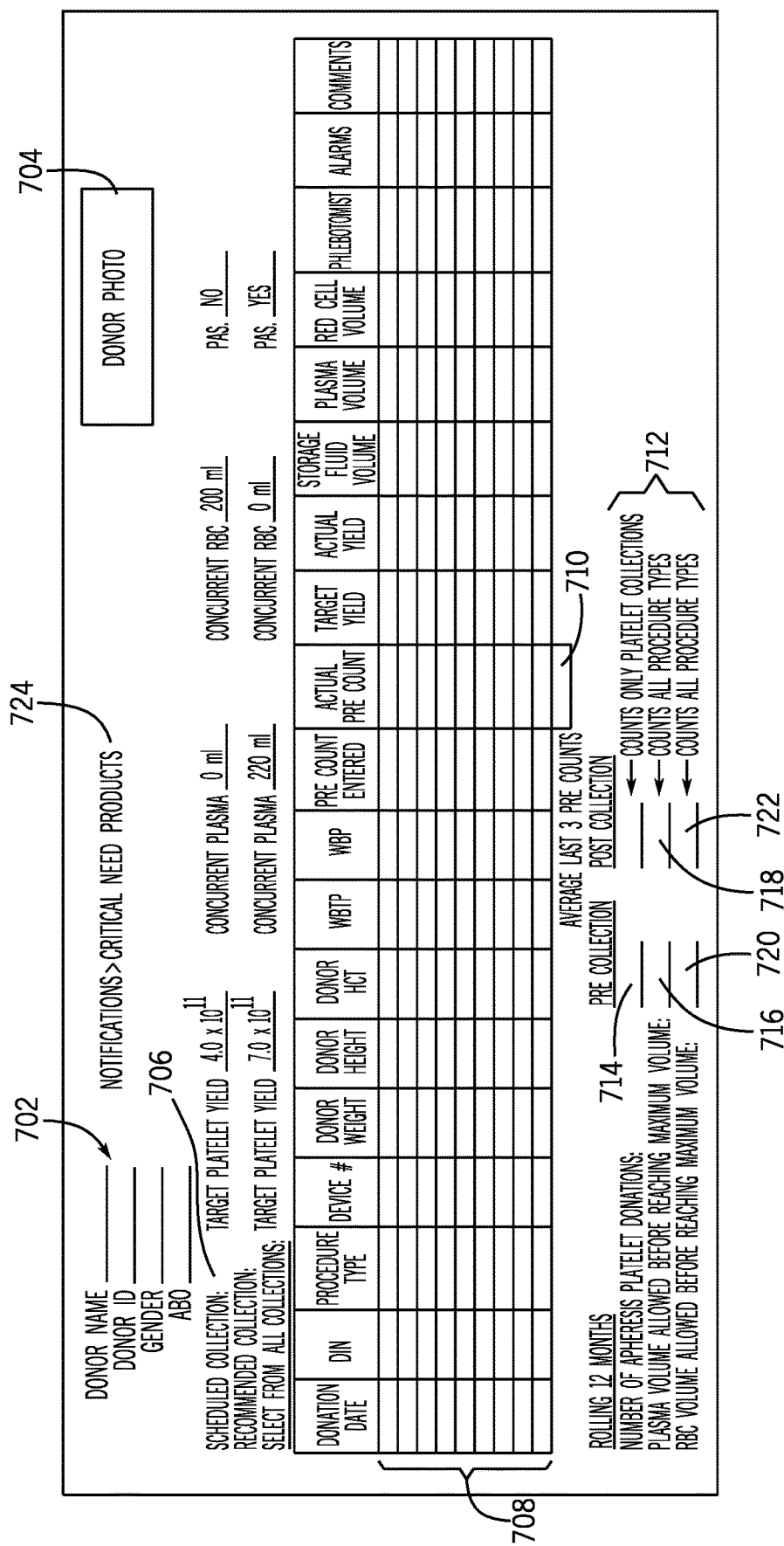
FIG. 7 is a screen shot of display data representing a donor history record summary, according to an exemplary embodiment.
Figure 7A:
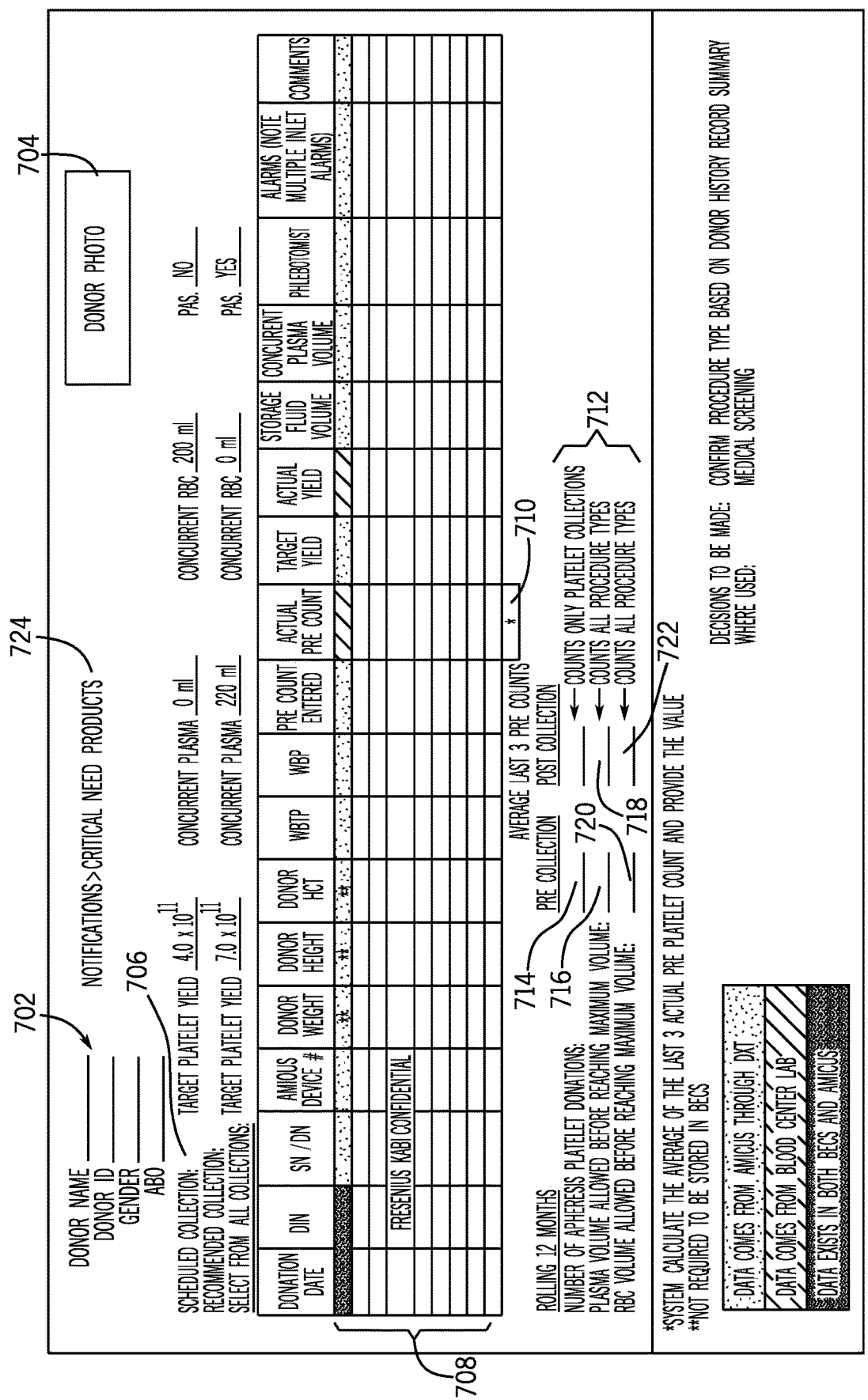
FIG. 7A is a screen shot of display data representing a donor history record summary, according to an alternative embodiment.
Figure 8:
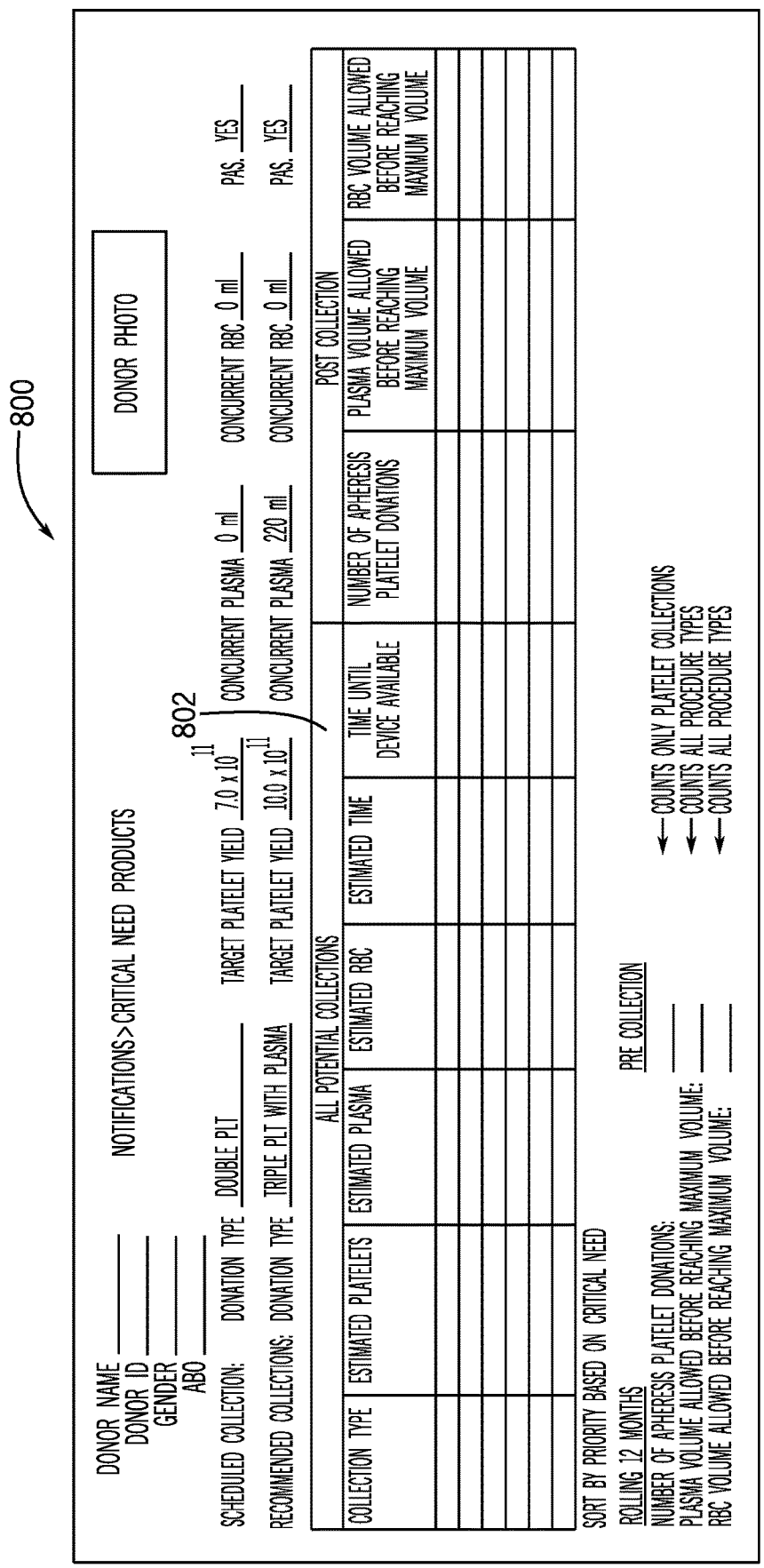
FIG. 8 is a screen shot of display data representing donor collection options, according to an exemplary embodiment.

Referring to FIG. 4, a process 400 of scheduling a donation type using a computing system is described, according to an exemplary embodiment. At a block 402, a donor CRM module 140 (FIG. 1) may be configured to provide a listing of donors and to facilitate scheduling of donors by way of the listing. At a block 404, a scheduling module (such as modules 150 and/or 160 of FIG. 1) is configured to receive a selection of a donor from a user. At a block 410, the scheduling module is configured to provide a screen, illustrated in FIG. 8, showing a view for a particular donor. The view may display donor profile information, such as name, ID, gender, ABO, etc., a donation type that the donor has been scheduled to make, and/or other information. At block 408, if additional insight is required by the user, additional donor information may be provided, such as a donor history record. Exemplary embodiments of donor history record screens are illustrated in FIGS. 7 and 7A. At block 410, all or a plurality of collection options may be viewed by the user. A user may view the donor history record at block 408. Additional information may be obtained by request from the user if additional insight is needed, which will move the process to block 414 to allow the user to review an Apheresis Procedure Record.

FIG. 7 illustrates display data representing a donor history record summary for a platelet donor, according to an exemplary embodiment. A donor profile data field 702 displays profile data for the donor. A donor photo 704 may be displayed to assist the user in matching the donor record being displayed to the donor being checked in or scheduled. A scheduled collection field 706 provides information regarding a blood component collection procedure that has been scheduled, which may include a target donation type (for example, Double PLT with cPlasma, 2 RBC, Whole Blood, 4 Plasma, etc.), target platelet yield in number of platelets, a plasma yield in milliliters, a RBC yield in mL, a Whole Blood yield in mL, an indication as to whether platelet additive solution (PAS) is to be used, yes or no, and/or other data.

A collection optimization algorithm may be programmed to make a recommendation as to the blood component collection which is more current than or based on more information than the scheduled collection plan. In the example illustrated in FIG. 8, the algorithm recommends a target triple platelet collection with concurrent Plasma using PAS instead of a double platelet collection with no concurrent products with PAS.

A collection optimization algorithm may take into account the blood center current inventory level, anticipated inventory demand, donor characteristics, device collection capabilities, etc. in making the recommendation.

Donation history data may be displayed in fields 708, with each field comprising data for a single donation event or occurrence. The donation history data may comprise donation date and donation ID, which may be obtained from the blood collection device and/or a Blood Establishment Computer Software (BECS) device and/or device data management system, Procedure Type such as Single Needle procedure (SN)/Double Needle procedure (DN), Amicus device number for the collection machine, donor weight, donor height, donor hematocrit or hemoglobin, pre-donation platelet count entered, actual pre-donation platelet count if average entered, target yield, actual yield, storage fluid volume, concurrent plasma volume, concurrent red cell volume, phlebotomist name, alarms, and/or comments. Donation history data may comprise data that comes from the blood collection device to a server computer configured to store the donation data in a database. Donation data such as actual pre-count and actual yield may come from a blood center lab, either electronically over a network or entered manually from a lab report. A BECS is an algorithm designed to be used in a blood collection facility and is intended for use in the diagnosis of disease or other conditions in donors, or in the prevention of disease in humans by preventing the release of unsuitable blood and blood components.

A field 710 comprises a calculation made by an algorithm of the average of the last 3 actual pre platelet counts. The calculated value is displayed to give additional information to the user scheduling the collection, and may be stored as part of the donor profile in a database. In the event there is a historical platelet count anomaly that is out of range, that value may be identified to not be used in the calculation made by the algorithm.

Fields 712 display pre-collection and post-collection donor eligibility as it relates to the rolling 12 month red cell and plasma volume loss allowed before reaching maximum volume and the number of remaining platelet donations allowed following regulatory guidelines. The remaining donations may be calculated based on historical donation data and one or more rules or other predetermined constraints regarding the number of donations of different types of blood components that may be made by a donor in a predetermined period of time. For example, if a donor is allowed to have 24 platelet collections in a year pursuant to regulation, policy, or otherwise, and the donor has already had 2 platelet collections within the past 12 months, field 714 will show 22 platelet collections remaining "pre collection" and 21 platelet collections remaining "post collection." The result is a subtraction made by a local or server-based algorithm based on data in the database in a blood donor's record. A workstation local to a user may be configured to transmit a request for the result of the subtraction to a server, which may be a computing device remote from the workstation (e.g., in another room, another building, another geographic location, etc.). In response, the server may be configured to transmit the result of the subtraction to the workstation.

Similarly, fields 716 and 718 may provide pre- and post-collection data of plasma volume allowed before reaching maximum plasma volume donation, again pursuant to a calculation of historical donations subtracted from a predetermined number of plasma volume allowed in a rolling 12 month period. For example, if a donor less than 175 pounds may donate 12 L of plasma in a rolling 12 month period pursuant to rule, regulation, policy, etc., and the user has made three individual donations of 0.73 L, 0.5 L and 0.73 L, the algorithm may calculate that 10.04 L of plasma volume are still allowed to be donated within the 12 month period. Fields 720 and 722 show the RBC volume allowed before reaching maximum volume in a rolling 12 month period pursuant to rule, regulation, policy, etc.

According to another feature, a notifications field 724 may be provided which may display an indication of blood component needs. These notifications may be generated by inventory modules 110 and/or 120 and provided to one or more workstations to assist the user in selecting the optimal procedure. The notifications may come in various forms of detail, such as "RBC needed," "0 positive RBC needed," etc., as well as providing an indication of the level of need, such as using color (e.g., red for critical need, yellow for moderate need, green for little need) or other indications (code 5 for critical need, code 3 or 4 for moderate need, code 1 or 2 for low need).

Referring to FIG. 7A, a donation history record summary is illustrated according to an alternative embodiment. Items which are similar to those in FIG. 7 are identified with the same reference numeral.

Referring to FIG. 8, an exemplary screen shot of display data representing donor collection options is shown. This display screen 800 may show some of the same data shown in the screen of FIG. 7, such as donor profile data, donor photo, rolling 12 month allowed collections, etc. An algorithm may be configured to calculate and display potential collections 802 and post collection rolling 12 month allowed collections based on each potential collection. For example, the algorithm may indicate that a platelet collection (collection type) may be performed with an estimated platelet yield (say 7.0×10 E11 based on an average of counts of previous donations), which will take an estimated time of 81 minutes (estimated time). The impact, post-collection, on the number of platelet donations will then decrease by one, and the plasma volume and RBC volume will be impacted using the estimated plasma volume and RBC volume associated with the collection type as Illustrated in 712. The pre-collection allowed volumes will remain unchanged. The algorithm may make similar indications for plasma donations, RBC donations, or any component combinations, based on data indicating average yield for a plurality of donors, average yield for this donor, estimated time for a plurality of donors, estimated time for this donor, etc.

The user may select one of the potential collections provided by the algorithm by, for example, clicking on the field. Returning to FIG. 4, at a block 412, the user may view a screen showing some or all available blood collection devices and statuses of devices in use. Blood collection facilities may have many networked blood collection devices which report their availability status to a server computer for use by the workstations in determining which device is available for a particular donor. Based on collection type selected, the user may select a device that will be reserved for the collection. The donor status is updated to reflect device reservation and desired collection type.

Once a donor completes an eligibility process, the user enters the donor parameters for that day's collection into the donor optimizer in block 410. The user confirms the collection type selected in the donor optimizer and sends the donor parameters to the selected device.

During and at the completion of the collection, at block 414, a record of the donation is created by the server, which may be populated with data about the new procedure (e.g., with data such as yields, duration of procedure, etc.).

According to one embodiment, the system does not store a total amount of one or more of the blood components the donor has donated over a predetermined period of time.

From the user's perspective, in a first step, a donor enters a facility and a user begins to review the schedule (FIG. 4, block 402). The user selects a donor to review and reviews all collection options for that donor (block 410). If additional insight is required, the user reviews a Donor History Record summary (408). If more insight is required, the user reviews an Apheresis Procedure Record (414). The user then chooses a donation type from the listed collection options (block 410). Once the donation type is known, the user views current statuses of devices (block 412) and makes a device selection for the selected procedure type and reserves the device (block 412). Donor status is updated to reflect the device reservation and desired procedure type. Next, the donor proceeds with a medical interview, which may include their donor history questionnaire, physical findings, etc. A user enters donor parameters into Donor Optimizer or loads donor parameters from BECS to Donor Optimizer. The user confirms donor procedure type in Donor Optimizer, then sends donor parameters to a remote server computer (called DXT). If the donor is eligible for the desired procedure type, the donor is moved to the reserved donation device. If the donor is not eligible for the desired procedure type, the donor is released. The user may select a different device for the next best optimal procedure type if applicable.

Figure 9:
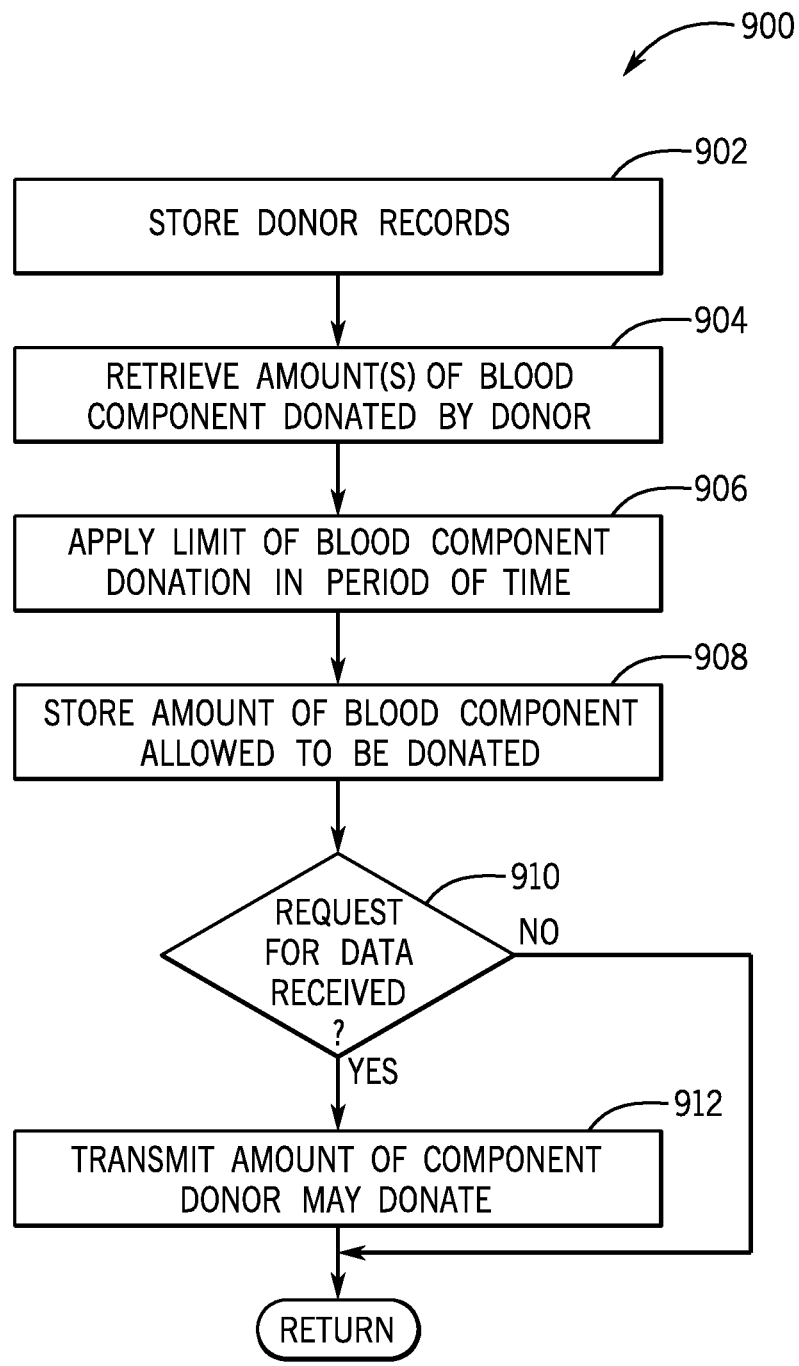
FIG. 9 is a flowchart of a method of tracking or scheduling blood donations, according to an exemplary embodiment.

Referring now to FIG. 9, a method of tracking or scheduling blood donations will be described according to an exemplary embodiment. A blood donation tracking system comprises a database storing records (block 902) for a plurality of blood donors. The records comprise data for a plurality of donations made by the blood donors, each record comprising an amount of a blood component donated. The amounts may be expressed in volume (e.g., plasma loss, blood loss, etc.), number of donations (e.g., platelet donations, etc.), or other units. At a block 904, a processing circuit coupled to the database may be configured to retrieve data representing an amount of blood components donated by a donor for one or more donations made. For example, if a donor has made three platelet donations over the past rolling 12 month period, the processing circuit will retrieve that information from the three donation records within the donor record. In various embodiments, the processing resources performing the blocks of FIG. 2 may be local to a scheduling computer, local to a server computer, provided elsewhere, or provided in a combination of processing resources.

At a block 906, the processing circuit may be configured to apply a limit of a blood component donation (e.g., red cell loss volume, plasma loss volume, the number of platelet donations, etc.) allowed over a predetermined period of time to determine the optimal collection type a donor may donate. The limit may be stored in server memory, client computer memory, the donor record, or elsewhere within the system. The limit may be updated from time to time based on policy of the health care facility, state or federal regulation, or other sources. The limit may be unique to the donor based on donor characteristics (e.g., height, weight, etc.) or may be the same for all or groups of donors. In one example, the limit may be 24 platelet donations in a rolling 12 month period. At block 906, the processing circuit may be configured to subtract 3 platelet donations that occurred within the trailing 12 month period from the 24 platelet donations allowed and to store (block 908) the amount of apheresis platelet donations allowed (21 platelet donations in this example). The amount may be stored in local memory, in the donor record, otherwise in the database, or elsewhere.

At a block 910, the processing circuit determines if a request for the amount of the blood component the donor may donate is received. If so, at a block 912, the processing circuit is configured to transmit the amount of blood component the donor may donate to the remote computing device from which the request was received, over a network.

The request may be part of a request from a scheduling computer for additional data from a donor record for use in generating a display screen for use in scheduling or otherwise selecting a blood component or components to be donated by a donor. In one example, the processing circuit is further configured to transmit data for a plurality of potential blood component collections to the remote computing device along with an indication of the amount of blood component that may be collected from the donor after each of the potential blood component collections. The plurality of potential blood component collections may be generated by the server based on one or more of a list of blood components the blood donation facility is designed to collect, donor characteristics, historical information about the donor's prior donations, the blood component needs of the blood donation facility, whether additional donations are allowed for this donor based on the determination made in blocks 904-908, and/or other factors.

The processing circuit may further be configured to generate and/or transmit display data indicating a need at a blood collection facility for a type of blood component. This data may be automatically generated by the server or another computer based on records in inventory module 110 (FIG. 1), manually entered by a user, received from a healthcare facility inventory module 120, and/or otherwise provided. The indication of need may comprise an indication of the criticality of the need in one more levels of criticality. In one advantageous embodiment, at least three levels of need are available for use in the notification, such as a great need, a moderate need, or a low need.

The processing circuit may further be configured to provide an indication of a pre collection amount of blood component the donor may donate and a post collection amount of blood component the donor may donate. The pre collection amount may represent the result of blocks 904-908 above and the post collection amount may represent that result minus a proposed blood component collection provided by the system as an option, selected by the user during a scheduling process, or otherwise provided to the system.

Figure 10:
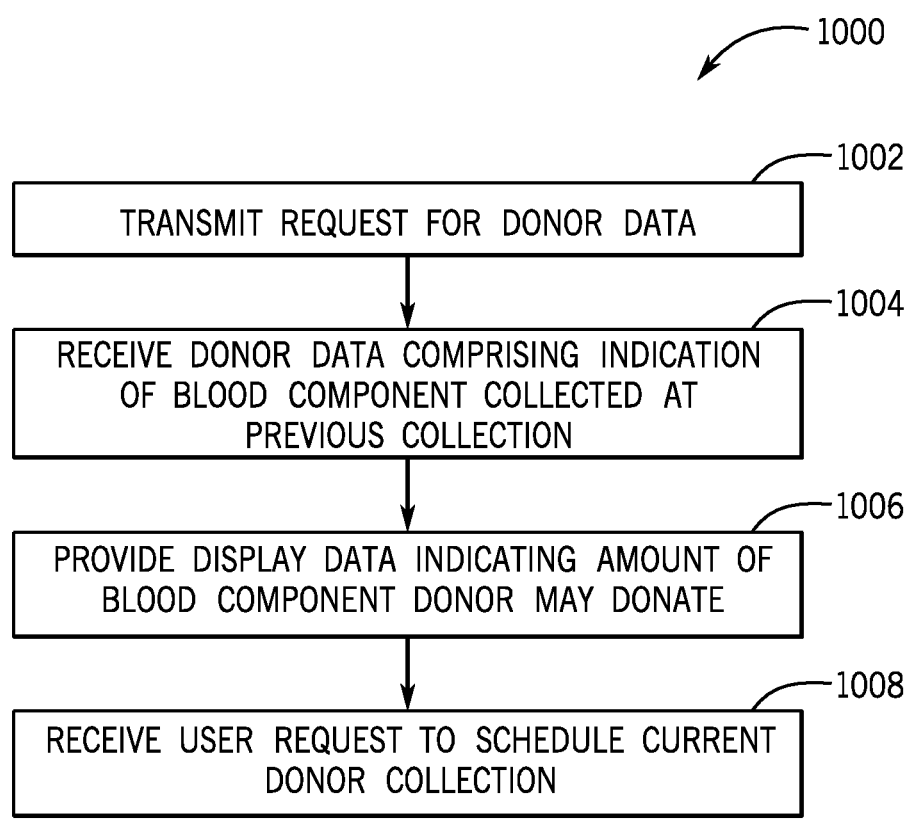
FIG. 10 is a flowchart of a method of tracking or scheduling blood donations, according to an exemplary embodiment.

Referring now to FIG. 10, another method of tracking or scheduling blood donations will be described according to an exemplary embodiment. The method may be operable on a client side computer, such as a workstation, scheduling computer, etc. At a block 1002, a user may use the computer to transmit a request for data from a donor record to a remote server computer over a network interface circuit. At a block 1004, the computer may be configured to receive the data from the donor record from the remote server computer. The data may comprise an indication of a blood component(s) collected at a previous donor collection. In one example, the data may comprise indications of one or more blood components collected at a plurality of previous donor collections, such as any of the data shown in FIG. 7. The data may comprise data for all previous collections for the selected donor, a sufficient number of prior donations to fill a screen such as the display screen shown in FIG. 7, an option for time-limited number of previous collections (e.g., 12 months trailing, 6 months trailing, etc.), etc. The data may comprise one or more of the data in the exemplary records shown in FIG. 7, such as donation date, DIN, counts, yields, alarms, etc. and may be obtained from one or a plurality of different sources.

At a block 1006, the computer may be configured to provide display data indicating an amount of the blood component(s) the donor may donate based on the indication of the blood component collected at a previous donor collection. The computer may make the necessary calculations of the amounts the donor may donate locally, or the calculations may be made remotely at a server computer. In either case, the computer may be configured to provide display data indicating the amount of the blood component(s) the donor may donate at a donor collection being currently scheduled or as needed prior to collection. Further, any of the data shown in FIG. 7 or 8, or other data, may be displayed at block 1006.

At a block 1008, the computer may be configured to receive a user request to schedule a current donor collection. The request to schedule may be a selection of a particular blood component type or procedure, a selection of one of a plurality of potential collections 802 (FIG. 8), and/or other parameters such as a selected blood collection device or location, a time of collection, whether PAS is to be used, etc.

Inventory

Figure 5:
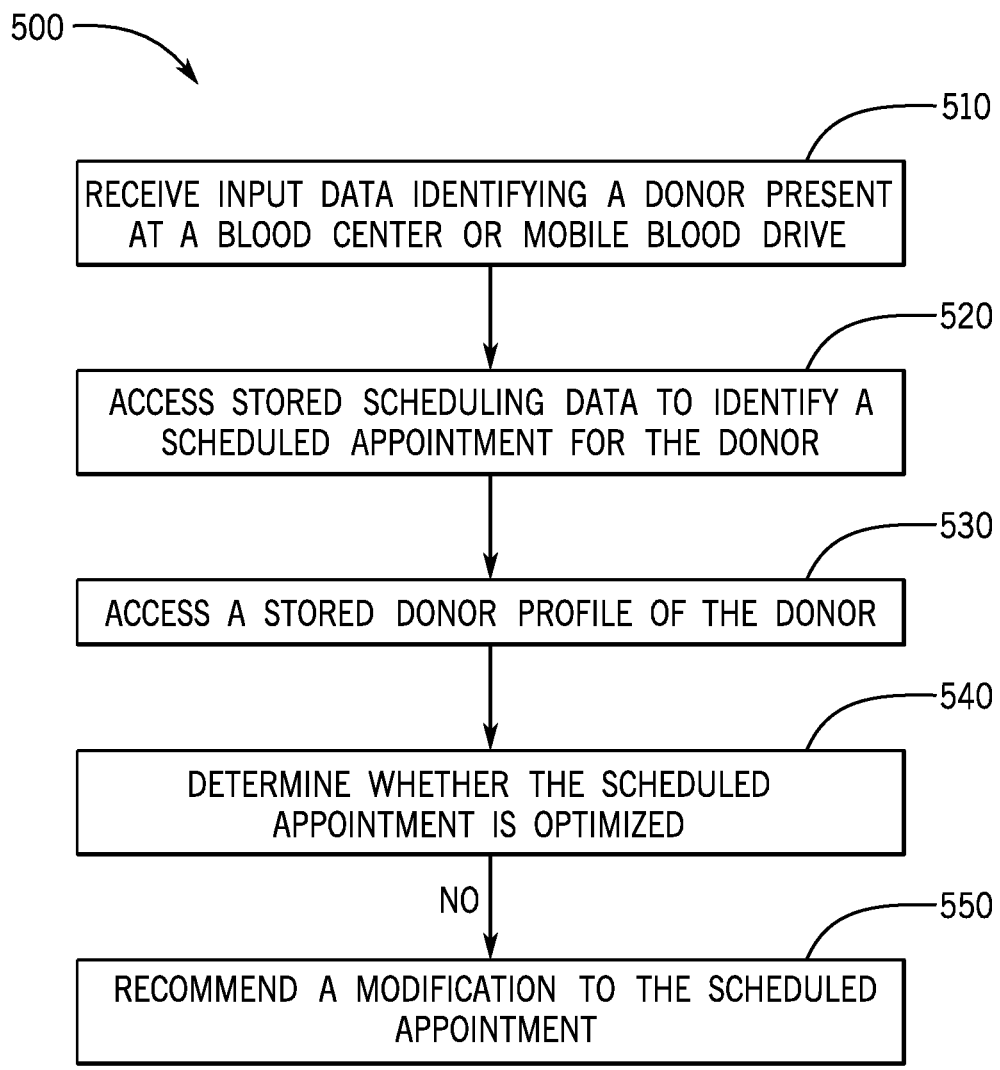
FIG. 5 is a flow chart illustrating a method of generating new blood component inventory to address anticipated or current demand in a blood component supply chain in accordance with another exemplary embodiment.

FIG. 5 depicts one embodiment of a method for generating new blood component inventory. Such a method may help coordinate new collections of blood components to better address anticipated or current demand or need in a blood component supply chain. As shown at block 510, in some embodiments, the blood component supply chain management system receives input data identifying a donor who presents himself or herself at a blood center or mobile blood drive. Upon arriving for blood donation, a donor may scan a donor-specific card or badge, which has identification information stored thereon, for example, in a magnetic strip, RFID tag, or barcode. Alternatively, the donor may be identified through biometric inputs such as a fingerprint or retinal scan. In other embodiments, the donor may enter donor-specific identification credentials such as a username, login ID, password, and/or pin into a blood center workstation to verify the donor's identify.

At block 520, the system may retrieve the donor's current appointment information by accessing scheduling data stored in a system database. At block 530, the system retrieves the donor's donor profile which is also stored in, and accessed through, a system database.

At block 540, the system may determine, at least in part from the scheduling data and the donor profile, whether the scheduled appointment is optimized. Donation optimization considerations include, for example, whether a donor is scheduled to donate the maximum number of blood components the donor is qualified to donate based on, for example, past donation history, the donor's current biographical information, and device capabilities. In some embodiments, the scheduled appointment is optimized if: the scheduled blood component is a needed blood component for which there is current or anticipated demand, and a donation potential of the present donor is maximized. Thus, in some embodiments, the system identifies one or more blood components for which demand exists or is imminent. This may be done, for example, by implementing an inventory assessment method. Alternatively, a health care facility staff member or blood center staff member may enter an input indicating which blood components are needed.

The one or more needed blood components are then compared to the blood component or components which the donor is scheduled to donate. The system may determine that the scheduled appointment is not optimized if the donor is not scheduled to donate a needed blood component but is eligible to donate such a product. Additionally, the system may assess, based for example, on the donor's gender, height, weight, and past donation history, whether the donor is able to donate more than he or she is scheduled to donate. For example, a donor may be scheduled to donate platelets, and to optimize the donation opportunity, the system will indicate the recommended number of treatment doses (i.e., the maximum safe number of doses) to collect, or the system may recommend an alternate collection type based on donor parameters, donation history, device opportunity, and inventory need. Similarly, a donor may be scheduled to donate Whole Blood when a double RBC donation and/or RBC and plasma donation is possible. In such a situation, the system may recommend a change in the appointment from Whole Blood collection to double RBC collection if the need for RBCs is greatest. The system may determine the scheduled appointment is not optimized if the donor is not scheduled to donate the maximum volume or number of products allowable.

At block 550, the system may recommend a modification to the scheduled appointment if the appointment is not optimized. In some embodiments of the method, recommending a modification to the scheduled appointment includes suggesting that collection of the scheduled blood component be either substituted with collection of the needed blood component or supplemented with collection of the needed blood component or an additional blood component. Various potential, recommended modifications to the collection may be presented to the donor or a blood center staff member prior to collection. Such a recommendation may need to be approved by a staff member and/or consented to by the donor. In one embodiment, the recommendations are presented on a touchscreen along with the currently scheduled collection regimen. The health staff member and/or donor may select the desired collection regimen. In some embodiments, a blood collection device will automatically begin the appropriate collection upon selection of the desired collection regimen. In other embodiments, the health staff member will set up the blood collection device to begin the appropriate collection.

Figure 6:
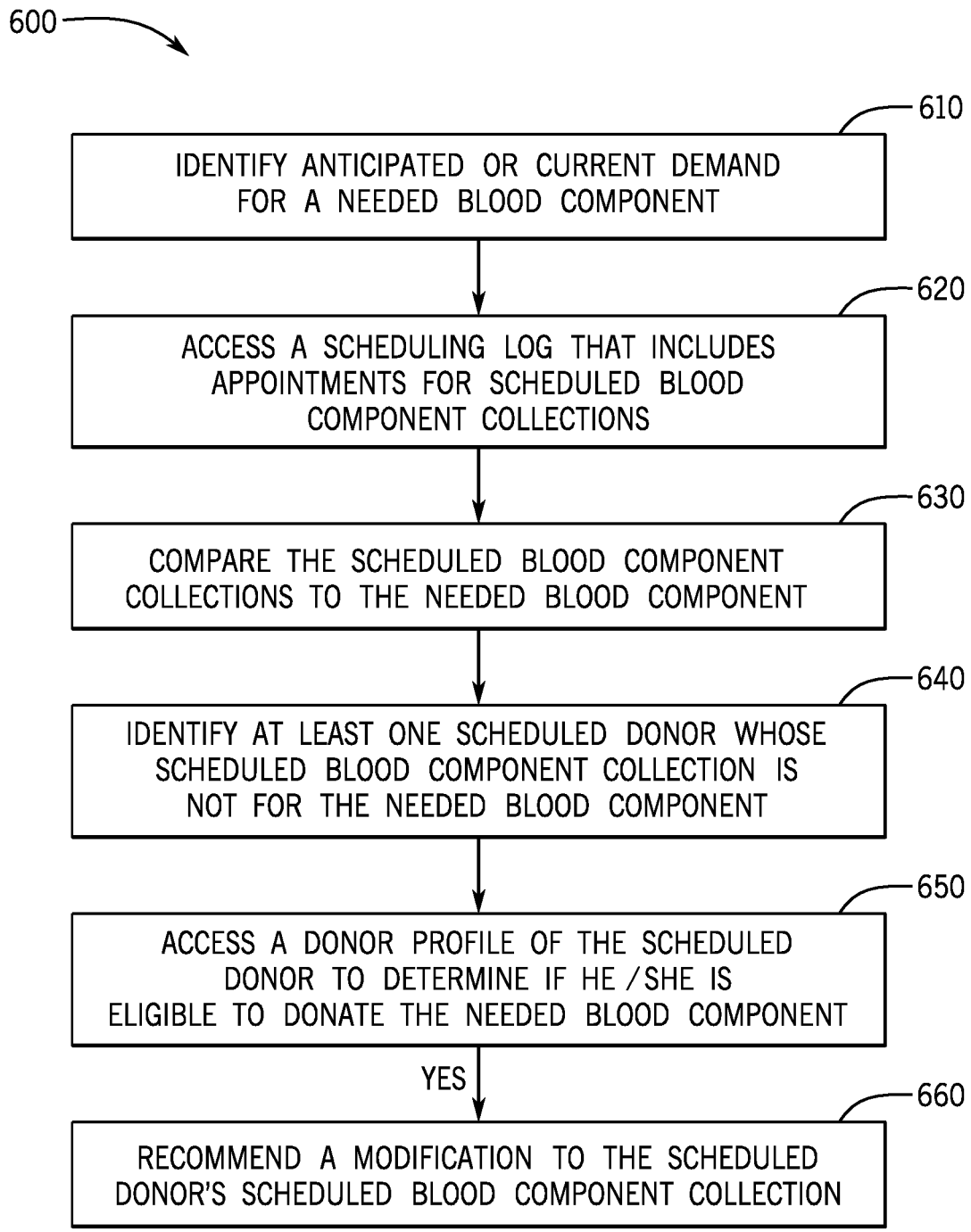
FIG. 6 is a flow chart of a method of generating new blood component inventory to address anticipated or current demand in a blood component supply chain in accordance with another exemplary embodiment.

FIG. 6 illustrates another embodiment of a method for generating new blood component inventory. Such a method 600 may be performed by a system in conjunction the method of FIG. 5 or independently. At block 610, the system identifies anticipated or current demand for one or more particular blood components. A blood component is referred to herein as a needed blood component when a current or imminent demand is determined to exist. The system may identify such demand by receiving an appropriate user input, such as an order for a blood component. Alternatively, the system may identify such demand by employing an inventory management algorithm.

At block 620, the system accesses a scheduling log from a system database. The scheduling log includes appointments for scheduled blood component collections. The system compares the scheduled blood component collections to the needed blood components in order to identify at least one scheduled donor whose scheduled blood component collection is not for a needed blood component, as shown at blocks 630 and 640.

In some embodiments, and as shown at block 650, the system accesses the donor profiles stored in the system's database for each of the scheduled donors whose scheduled blood component collection is not for a needed blood component. The system reviews the biographical information and donation history stored in each donor profile to determine whether a scheduled donor is eligible to donate a needed blood component. For example, to be eligible, a scheduled donor of a particular gender will meet the device criteria, for example, for double RBC donations, the scheduled donor will meet hemoglobin count, height, and weight requirements; moreover, a specified amount of time will have passed since the scheduled donor last donated. At block 660, the system recommends a modification to the scheduled donor's scheduled blood collection if the scheduled donor is eligible for a modification.

Computing Systems

Figure 3:
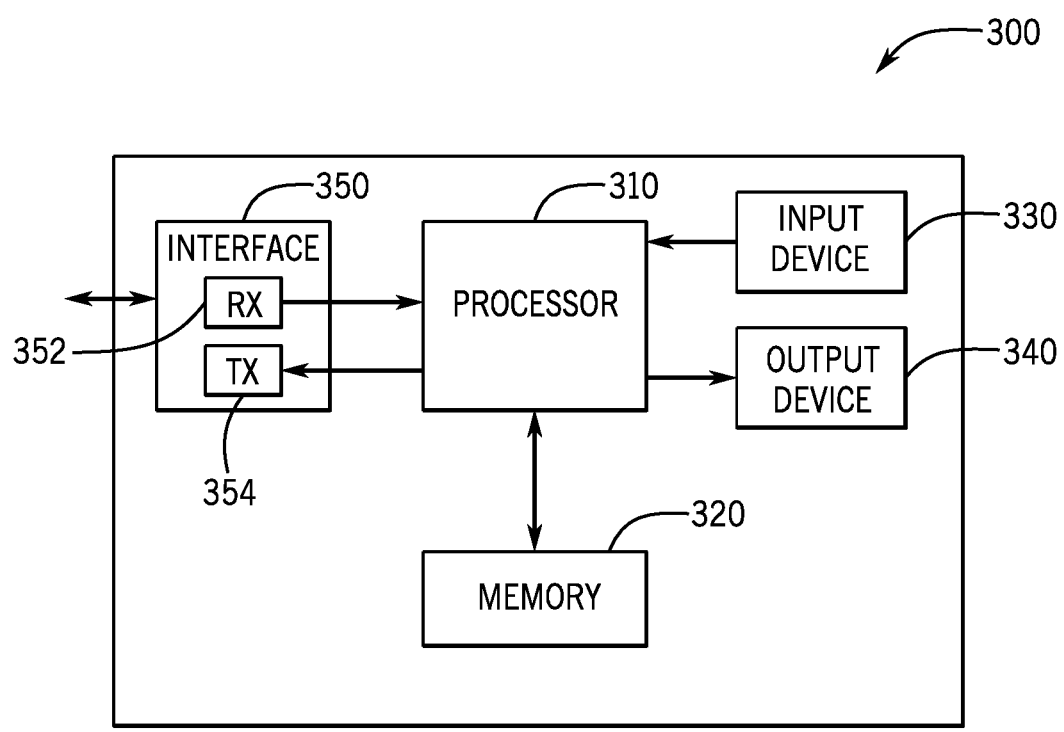
FIG. 3 is a general schematic block diagram of a blood component supply chain management system in accordance with another exemplary embodiment.

Referring to FIG. 3, one or more of the computing devices described herein may comprise components illustrated in FIG. 3. The computing device 300 may include a memory 320 configured to store data and instructions; a processor 310 configured to execute the instructions stored in memory to implement an operating system and various system functions; and a communication interface 350 configured to receive information from, and transmit information to, remote devices. The memory may be a storage device coupled to a processor and/or may be integral to the processor.

The processor 310 can be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The processor 310 may also be implemented as a combination of computing devices, e.g., a combination of a DSP and a microprocessor, a plurality of microprocessors, one or more microprocessors in conjunction with a DSP core, or any other such configuration.

The memory 320 stores a set of instructions, in the form of software code, which the processor 310 is configured to execute. Additionally, the memory may be configured to store data received from remote devices via the communication interface 350. The storage devices can also include a disk drive, for example, a hard disk drive. Other volatile or non-volatile storage devices may additionally or alternatively be used, including optical discs, floppy discs, magnetic tape, and Zip drives.

The processor 310, in conjunction with software stored in the memory 320, may execute an operating system, such as, for example, a Windows, UNIX, Mac OS, or Solaris operating system. The processor 310 also executes software applications stored in the memory 320. The software applications may include code written in any suitable programming language known to those skilled in the art, including, for example, Java and C++ programming languages. In some embodiments, the memory 320 includes software for operating the computing system 300 as a web server.

The network interface 350 to which the processor 310 is coupled, via, for example, the system bus, includes both a receiver 352 and a transmitter 354.

The computing system 300 may include one or more input devices 330 and/or output devices 340 coupled to the processor 310. Such devices may enable a system administrator to enter inputs into, and receive outputs from, the system 300. Input devices may include, for example, a keyboard, mouse, touchscreen, button, switch, and/or microphone, and output devices may include, for example, a display, printer, or speakers.

In the above detailed description, reference is made to the accompanying drawings, which form part of the present disclosure. The embodiments described in the drawings and description are intended to be exemplary and not limiting. Other embodiments may be utilized and modifications may be made without departing from the spirit or the scope of the subject matter presented herein. Aspects of the disclosure, as described and illustrated herein, can be arranged, combined, and designed in a variety of different configurations, all of which are contemplated and form part of this disclosure. The term "comprising" or "comprises" is intended to mean that the devices, systems, and methods include the recited elements, and may additionally include any other elements. The singular form "a," "an" or "the" include both singular and plural elements. For example, and without limitation, "a blood component" includes one or more blood components, and "a donor" may refer to one or a plurality of donors.

The invention claimed is:

1. A blood donation collection system comprising: a blood collection device configured to perform an apheresis function to collect blood components:
a database storing records for a plurality of blood donors, the database comprising records for a plurality of donations made by the blood donors, each record comprising an amount of a blood component the blood donor has donated;
a remote computing device remote from the database;
a network interface circuit configured to receive data over a network relating to the donations made by the blood donors and the records associated with those donations including donor characteristics, and configured to communicate data over the network to the remote computing device;
a processing circuit coupled to the database and the network interface circuit configured to:
determine an amount of blood component a donor may donate based on records for a plurality of donations made by the blood donor and based on a limit of an amount of blood component a donor may donate in a predetermined period of time;
receive a request for the amount of the blood component the donor may donate from the remote computing device; and
transmit the amount of the blood component the donor may donate to the remote computing device;
provide an indication of the amount as a pre collection blood component amount the donor may donate and further providing an indication of a post collection blood component amount the donor may donate, wherein the post collection blood component amount the donor may donate represents the pre collection blood component amount the donor may donate minus an amount of a blood component collection selected by a user during a scheduling process at the remote computing device; and
transmit the indications to the remote computing device;
wherein the remote computing device is configured to:
display a plurality of blood collection procedure options on a display;
display the indication of the amount as a pre collection blood component amount the donor may donate on the display;
display the indication of the post collection blood component amount the donor may donate for each of the plurality of blood collection procedure options;
receive a user selection of one of the blood collection procedures;
transmit instructions for the selected blood collection procedure to a blood component collection device, wherein the blood component collection device collects a blood component from a donor using the instructions.

2. The blood donation collection system of claim 1, wherein the processing circuit is further configured to store the amount of the blood component the donor may donate in the donor record in the database.

3. The blood donation collection of claim 1, wherein the processing circuit is further configured to transmit data for the plurality of potential blood component collection options to the remote computing device along with an indication of the amount of blood component the donor may donate after each of the potential blood component collections.

4. The blood donation collection system of claim 1, wherein the predetermined period of time is a rolling 12 months or a time period otherwise defined by the user.

5. The blood donation collection system of claim 1, wherein the system does not store a total amount of blood the donor has donated over a predetermined period of time.

6. The blood donation collection system of claim 1, wherein the records for the plurality of donations made by the blood donors comprises records for blood components comprising plasma, red blood cells, platelets, whole blood or any combination of the blood components.

7. The blood donation collection system of claim 1, wherein the indication of the blood component a blood donor has donated comprises an indication that the donor has made a blood donation, whether a complete or incomplete donation comprising any combination of blood components.

8. The blood donation collection system of claim 1, wherein the processing circuit is further configured to generate display data indicating a need at a blood collection facility for a type of blood component to be collected.

9. The blood donation collection system of claim 8, wherein the processing circuit is further configured to provide an indication of a level of need selected from at least three levels.

10. A blood donation collection system, comprising:
a blood collection device configured to perform an apheresis function to collect blood components;
a database storing records for a plurality of blood donors;
a network interface circuit configured to receive data over a network relating to donations made by the blood donors and configured to communicate the data over the network to a remote computing device;
a server computer comprising a processing circuit coupled to the database and the network interface circuit configured to:
receive from the remote computing device data indicative of a scheduled blood component collection;
run a collection optimization algorithm to make a recommendation as to a recommended blood component collection;
transmit the recommended blood component collection to the remote computing device for display;
receive an indication of a number of platelet donations a blood donor has donated;
receive an indication of a volume of a blood component a blood donor has donated;
retrieve from the database a number of platelet donations the donor may donate in a predetermined period of time;
retrieve from the database a volume of the blood component the donor may donate in the predetermined period of time;
subtract from the number of platelet donations the donor may donate in the predetermined period of time the number of platelet donations the blood donor has donated;
subtract from the volume of blood component the donor may donate in the predetermined period of time the volume of the blood component the blood donor has donated;
store a result of the subtractions in the database in a blood donor record;
receive a request for the results of the subtractions from the remote computing device;
transmit the results of the subtractions to the remote computing device;
generate at least one post collection amount of blood component by subtracting at least one of a number of platelet donations and a volume of blood component associated with the recommended blood component collection from the result of the subtractions;
provide an indication of the at least one post collection amount to the remote computing device; and
wherein the remote computing device is configured to:
display an indication of the recommended blood component collection and at least one other blood component collection;
display the indication of the at least one post collection amount;
receive a user selection of the recommended blood component collection or the at least one other blood component collection, wherein the remote computing device or the server computer is configured to transmit instructions for the selected blood component collection to the blood component collection device, wherein the blood component collection device collects a blood component from a donor using the instructions.

11. The blood donation tracking collection of claim 10, wherein the processing circuit is further configured to identify if a donor does not qualify for a collection type based on the volumes of blood component the donor has donated in the predetermined period of time and the number of platelet donations made in the predetermined period of time.

12. The blood donation tracking collection of claim 10, wherein the predetermined period of time is approximately rolling 12 months.

13. The blood donation tracking collection of claim 10, wherein the system does not store a total amount of any blood component the donor has donated over a predetermined period of time.

14. The blood donation collection system of claim 10, wherein the predetermined period of time is a rolling period of time, such that the volume of blood component donated or the platelet donation donated are omitted from the subtraction during a future calculation.

15. The blood donation collection system of claim 10, wherein the results of the subtractions are provided as display data which is sorted based on an indication of need for all blood components and optimizing donor characteristics and device capabilities to collect the optimal blood components at a blood collection facility.

16. The blood donation collection system of claim 1, wherein the post collection blood component the donor may donate is calculated based at least in part on an estimated volume of previous donations.

17. A blood donation collection system, comprising:
a blood collection device configured to perform an apheresis function to collect blood components;
a database storing records for a plurality of donors, the database comprising records for a plurality of donations made by the donors, each record comprising an amount of a blood component the blood donor has donated;
a remote computing device remote from the database;
a network interface circuit configured to receive data over a network relating to the donations made by the blood donors and configured to communicate data over the network to the remote computing device;
a first processing circuit coupled to the database and the network interface circuit configured to:
receive a request from the remote computing device for data from the processing circuit;
determine a number of platelet donations a donor may donate based on the records and based on a limit of a number of platelet donations the donor may donate in a predetermined period of time;

determine a volume of plasma the donor may donate based on the records and based on a limit of a volume of plasma the donor may donate in the predetermined period of time;

run a collection optimization algorithm to generate a plurality of potential blood component collections;

determine a number of platelet donations remaining post collection for each of the plurality of potential blood component collections;

determine a volume of plasma remaining post collection for each of the plurality of potential blood component collections;

the remote computing device comprising a second processing circuit configured to:

transmit the request for data to the first processing circuit;

receive the number of platelet donations the donor may donate, the volume of plasma the donor may donate, the potential blood component collections and the number of platelet donations remaining post collection and volume of plasma remaining post collection for each of the potential blood component collections;

generate display data for a display screen displaying the number of platelet donations the donor may donate, the volume of plasma the donor may donate, the potential blood component collections and the number of platelet donations remaining post collection and volume of plasma remaining post collection for each of the potential blood component collections; and receive a user selection of one of the potential blood component collections, wherein the first processing circuit or second processing circuit is configured to transmit instructions for a blood component collection procedure based on the selected one of the potential blood component collections to the blood collection device, wherein the blood collection device is configured to use the instructions to perform the blood component collection procedure to collect the blood components.

18. The blood donation collection system of claim 17, wherein the second processing circuit is configured to generate display data for the same display screen comprising donor name, donor gender and donor blood type for the donor.

19. The blood donation collection system of claim 18, wherein the second processing circuit is configured to generate display data for the same display screen wherein potential blood component collections are sorted based on an indication of need for different blood components at a blood collection facility.

* * * * *